United States Patent [19]

Wunsch

[11] Patent Number: 4,512,764
[45] Date of Patent: Apr. 23, 1985

[54] MANIFOLD FOR CONTROLLING ADMINISTRATION OF MULTIPLE INTRAVENOUS SOLUTIONS AND MEDICATIONS

[76] Inventor: Richard E. Wunsch, 207 Circle Dr., Traverse City, Mich. 49684

[21] Appl. No.: 423,978

[22] Filed: Sep. 27, 1982

[51] Int. Cl.³ .............................................. A61M 5/14
[52] U.S. Cl. ........................................ 604/80; 604/83; 604/250; 138/118; 222/145
[58] Field of Search ............... 604/34, 80, 86, 151, 604/173, 250, 81, 284, 83; 138/118; 251/8; 128/DIG. 12; 222/145, 330

[56] References Cited

U.S. PATENT DOCUMENTS

| | | | |
|---|---|---|---|
| 2,710,004 | 6/1955 | Stamper | 604/80 |
| 2,925,814 | 2/1960 | Vibber et al. | 604/66 |
| 2,954,028 | 9/1960 | Smith | 604/80 |
| 2,962,193 | 11/1960 | Totten | 604/81 X |
| 3,043,303 | 7/1962 | Still | 604/66 |
| 3,217,711 | 11/1965 | Pecina et al. | 604/81 |
| 3,411,534 | 11/1968 | Rose | 604/250 X |
| 3,886,937 | 6/1975 | Bobo et al. | 604/81 |
| 3,941,126 | 3/1976 | Dietrich et al. | 604/80 |
| 3,982,534 | 9/1976 | Buckman | 604/81 |
| 3,993,054 | 11/1976 | Newman | 604/153 X |
| 4,034,754 | 7/1977 | Virag | 604/81 |
| 4,094,318 | 6/1978 | Burke et al. | 604/65 |
| 4,184,815 | 1/1980 | Casson et al. | 417/477 |
| 4,191,183 | 3/1980 | Mendelson | 604/80 |
| 4,219,022 | 8/1980 | Genese | 604/81 |
| 4,236,515 | 12/1980 | Genese | 604/81 |
| 4,237,880 | 12/1980 | Genese | 604/81 |
| 4,250,879 | 2/1981 | Muetterties | 604/81 |
| 4,256,103 | 3/1981 | Mylrea | 604/81 |
| 4,256,104 | 3/1981 | Muetterties et al. | 604/81 |
| 4,256,105 | 3/1981 | Leahey et al. | 604/81 |
| 4,258,712 | 3/1981 | Harms et al. | 604/81 |
| 4,312,993 | 1/1982 | Stauffer | 604/34 X |
| 4,425,113 | 1/1984 | Bilstad | 604/34 X |

Primary Examiner—Stephen C. Pellegrino
Attorney, Agent, or Firm—Cullen, Sloman, Cantor, Grauer, Scott & Rutherford

[57] ABSTRACT

A manifold for sequentially dispensing a plurality of solutions through an intravenous supply catheter. The manifold includes a disposable tubing manifold that is connected to each of the solutions to be administered. Flow of solution through the branches of the tubing manifold can be stopped by valves which engage each branch. The quantity of solution dispensed is metered by a volumetric infusion pump and controlled by sequentially opening and closing the valves individually.

8 Claims, 3 Drawing Figures

MANIFOLD FOR CONTROLLING ADMINISTRATION OF MULTIPLE INTRAVENOUS SOLUTIONS AND MEDICATIONS

BACKGROUND OF THE INVENTION

1. Technical Field

The present invention relates to a manifold for administering intravenous solutions and medications. More particularly, the invention relates to a manifold for sequentially supplying a plurality of solutions to a single intravenous tube.

2. Prior Art

Medical treatment frequently requires the administration of more than one solution or medication by intravenous injection. In many medical treatments several drugs are administered periodically.

To minimize the number of injections given to a patient it is common practice to inject medications through a single intravenous tubing by means of one or more Y-connectors. The normal procedure is for a member of a hospital staff to unsheath a needle and insert it in a Y-connector at time periods and in quantities specified by the treating physician. When a given medication has been administered the needle is removed from the Y-connector, resheathed and stored next to the patient's bed until the next treatment interval. This procedure is subject to contamination due to the repeated sheathing and unsheathing of the needle. While this procedure is acceptable when a limited number of medications are administered, as the frequency of administration increases the amount of staff time expended, difficulty of keeping the needle and Y-connector sterile, and chance of error in administering a medication likewise increase.

This procedure for periodically administering medication to patients is time consuming for hospital staff and requires detailed instructions because medication is often prescribed around the clock. In medical treatments requiring a large number of solutions each having a loosely hanging tube, a member of the hospital staff could conceivably be confused and dispense the wrong solution.

Frequently, tubes are left dangling loosely around the patient's bed, instead of being tied out of the way, because the tubes must be free for connection to the Y-connector. The tubes can be caught in the side rails of the bed and damaged. During administration of a solution one of the tubes may be pinched off inadvertently resulting in insufficient medication being dispensed.

Various types of manifolding apparatus have been developed to meet the problems posed by supplying multiple medications to a patient. U.S. Pat. No. 2,954,028 to Smith discloses such an apparatus for administering parenteral fluids through the use of a manifold. While the Smith manifold allows a large number of medications to be administered simultaneously, it is bulky and time consuming to set up. The different medications in the various passages of the manifold may intermix and if not compatible could interact deleteriously with each other. Different branches of the manifold open into the central tube at directly opposite locations which allows the fluids to flow from one branch into another.

Reuse of the Smith manifold is subject to several drawbacks. It is well known that some medications, while theraputic for some, are toxic to other patients. If a patient receives medication through a manifold residual deposits of a previously administered medication may be present in the manifold. If the residual deposit is a substance that is toxic to the patient it is possible that the patient could be harmed. Therefore, unless the manifold is cleaned and sterilized between each patient, there is a danger that a patient may inadvertently receive residue from a medication administered to a prior patient. Cleaning and sterilizing the manifold between uses is laborious and requires valuable staff time.

In addition, prior art devices have failed to disclose an accurate method for sequentially metering several different medications through a common catheter that is both inexpensive and simple to use. While visual sight glass drop counters have been used with Y-connectors, as shown in U.S. Pat. No. 3,886,937 to Bobo et al and in the Smith manifold described above, such devices are time consuming to use and must be visually monitored for accuracy. Electronic drop counters as disclosed in U.S. Pat. No. 4,094,318 to Burke offer improved accuracy but are extremely expensive, especially if more than one or two solutions are to be administered.

These and other problems are solved simply and efficiently by the present invention.

SUMMARY OF THE INVENTION

The multiple intravenous solution manifold of the present invention comprises a three-piece manifold valve assembly having a disposable tubing manifold that assures sterility and purity in medications dispensed to a patient. The three part manifold apparatus is simple to disassemble for removing the disposable tubing manifold and replacing it with a new sterile tubing manifold.

The remainder of the manifold valve assembly does not contact any medication and therefore may be safely used repeatedly by different patients. Since the only portion of the valve manifold assembly that contacts more than one medication is the tubing manifold, there is no hazard of residual medication being administered to subsequent patients.

The manifold plate has a plurality of valves with each valve being operative to close off the flow of a solution through a branch of the tubing manifold to control the flow of the solutions to the patients. The use of a manifold valve apparatus eliminates the need to sheath and unsheath medication needles from individual solutions to connect them to Y-tubing connectors. Therefore, the present invention offers improved sterility because the tubing is handled only when a solution bottle is replaced.

The manifold valve assembly also eliminates the unsightly and confusing loosely dangling tubes of the prior art by allowing the solution tubes to remain attached to the apparatus when not in use. Instructions from physicians to hospital staff can be simplified since each channel of the apparatus can be clearly identified. The tubing may be conveniently tied together out of the way of the hospital staff and the patient because the tubes do not need to be handled as often.

The dispensing tube of the valve manifold is preferably connected to an infusion pump that in turn pumps the intravenous solution at a measureable rate into a patient by means of an intravenous needle or catheter. At any one time it is preferred that only one valve will be open to allow the solution to be accurately measured as it is dispersed. The infusion pump draws solution at a known flow rate for a prescribed period of time, whereby the medication dose may be easily and accurately measured. A tube for a keep open solution, or base solution, is connected to one end of the valve manifold for use when no medication is being dispensed to prevent the formation of clots in the catheter or in the patient's vein at the injection point.

The present invention will be better understood after studying the attached drawings in view of the following detailed description of the invention.

DETAILED DESCRIPTION

Figure 1:
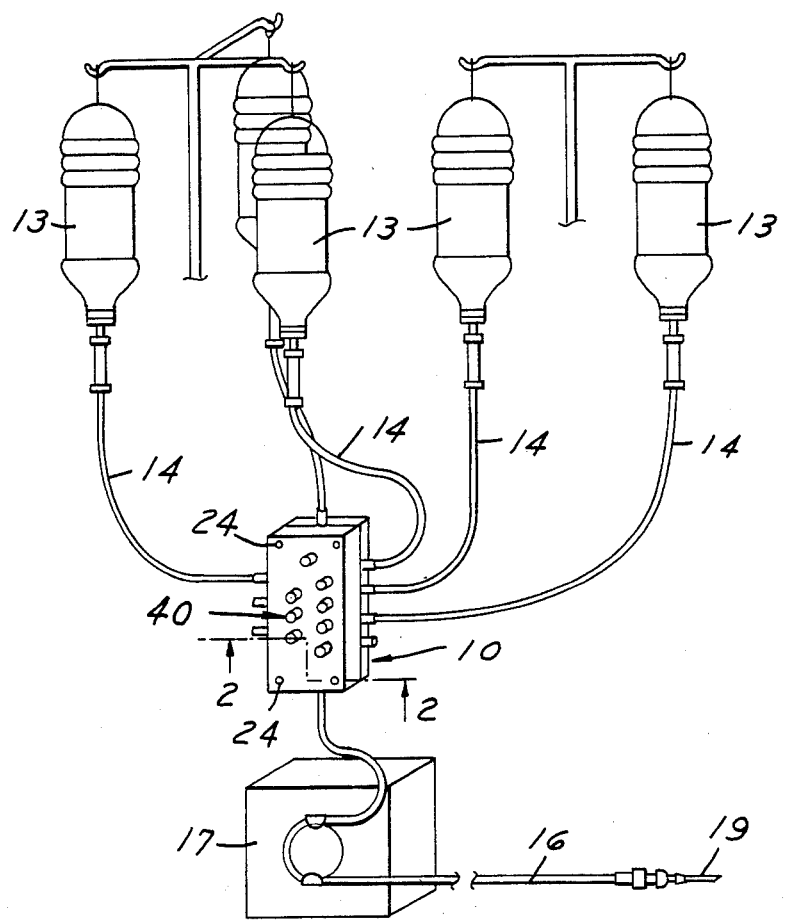
FIG. 1 is an elevational view of the manifold connected to several solution containers and an infusion pump.

Referring now to FIG. 1, the multiple intravenous solution manifold assembly is generally indicated by the reference numeral 10. The manifold 10 is used to intravenously dispense a plurality of medications and solutions to a patient. The intravenous solutions are contained in a plurality of bottles 13 that are connected to the manifold 10 by means of supply tubes 14. Solutions passing through the manifold 10 are sequentially administered by means of the dispensing tube 16 which is powered and controlled by an infusion pump 17. Medication is injected into a patient by means of a catheter or intraveous needle 19.

Figure 2:
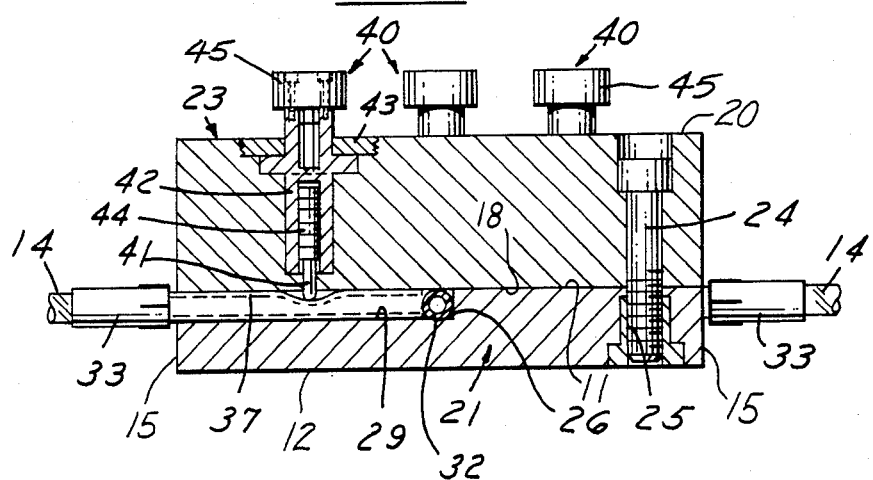
FIG. 2 is a sectional view of the manifold taken along the line 2—2 in FIG. 1.
Figure 3:
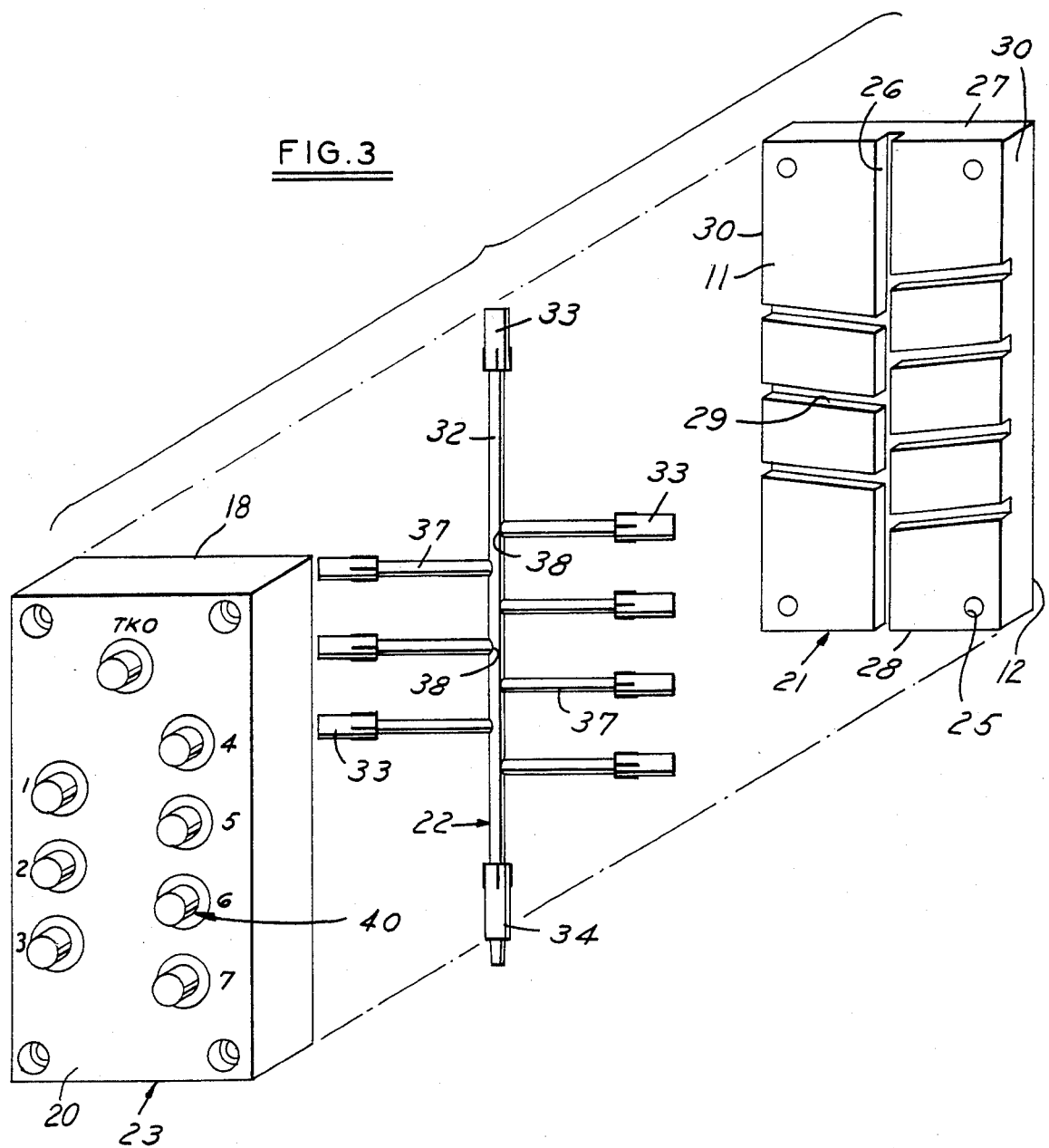
FIG. 3 is an exploded perspective view of the three part valve manifold assembly.

The intravenous solution manifold assembly 10 of the present invention is described in detail with reference to FIGS. 2 and 3. The manifold assembly 10 includes a manifold plate, generally indicated by the numeral 21, which receives the tubing manifold 22 and is covered by the valve plate 23. The entire manifold assembly 10 is secured together by means of a plurality of bolts 24 that are removably received within threaded openings 25 formed in the manifold plate 21. If desired, the threaded openings 25 may include a nut or other threaded reinforcement member.

The manifold plate 21 is a rigid member and has a pair of generally flat inner and outer surfaces 11 and 12 respectively and a pair of side surfaces 15. Inner surface 11 has a vertical slot 26 running the length of the manifold plate 21 from the top or end surface 27 to the bottom or end surface 28. The vertical slot 26 is a U-shaped channel opening on the face or inner surface 11 of the manifold plate 21. Branch slots 29 are formed in the manifold plate 21 to extend from the vertical slot 26 to the lateral sides 30 of the manifold plate 21. The branch slots 29 are U-shaped channels that open onto the face of the manifold plate 21. The branch slots 29 extend from the vertical slot 26 at a slightly acute angle relative to the portion of the vertical slot extending toward the top 27 of the manifold plate 21.

The tubing manifold 22 is made up of the trunk tube 32 that extends from the top 27 to the bottom 28 of the manifold plate 21. The trunk tube 32 includes a female connector 33 on its top end and a male connector 34 on its bottom end. A plurality of branch tubes 37 extend from opposite sides of the trunk tube 32 from longitudinally spaced openings 38 formed in the trunk tube. The branch tubes open into the trunk tube 32 to permit fluid flow from the branch tubes 37 to the trunk tube 32. The branch tubes 37 intersect the trunk tube 32 at spaced locations so that fluid flow is directed into the trunk tube 32 and not into another branch tube 37.

When the tubing manifold 22 is placed in the manifold plate 21 the branch tubes 37 are fit into the branch slots 29 while the trunk tube 32 fits into the vertical slot 26. The branch tubes 37 in their free state extend perpendicularly from the trunk tube 32. However, when the tubing manifold 22 is placed in the manifold plate 21, the branch tubes 37 are bent into the inclination of the branch slots 29. By so doing, fluid flow in the branch tubes from the lateral sides 30 to the trunk tube 32 is encouraged by gravity while fluid flow in the opposite direction is resisted by gravity.

The valve plate 23 has a pair of generally flat inner and outer surfaces 18 and 20 respectively and includes a plurality of valves 40 which are used to selectively stop fluid flow through the branch tubes 37 and the trunk tube 32. The valves 40 includes a wedge 41 which is positioned to bear upon one of the branch tubes 37 or the trunk tube 32. The wedge 41 is connected to internally threaded valve stem 42 that is retained in the valve plate by means of a packing nut 43. The valve stem receives a valve shaft 44 which is attached to the wedge 41 for moving the wedge 41 longitudinally relative to the internally threaded valve stem 42. A knob 45 is provided on the internally threaded valve stem 42 to permit operation of the valve 40.

Each of the valves 40 has an open position in which fluid flow is permitted through the tube 37 and a closed position in which the wedge 41 is pressed against the tube 37 to prevent fluid flow through the branch tube 37. A valve 40 is also provided on the trunk tube 32 for shutting off the keep open solution. The valve 40 engaging the trunk tube 32 operates in the same manner as each of the valves 40 engaging the branch tubes 37.

In operation, the solution bottles 13 are hung above the valve manifold apparatus 10 so that solution flows from the bottles 13 to the apparatus 10 through the supply tubes 14. The supply tubes 14 are received within the female connectors 33 that extend from the top 27 of the manifold plate 21 in fluid flow connection with the trunk tube 32. Other supply tubes 14 are received within female connectors 33 that are attached to each of the branch tubes 37 and extend from the lateral sides 30 of the manifold plate 21. Each I.V. solution flows from the bottles 13 to the apparatus 10. The flow of the I.V. solution into the dispensing tube 16 is controlled by means of the valves 40. Each of the valves 40 has an open position in which fluid is permitted to flow from the supply tubes 14 into the dispensing tube 16 and a closed position in which the branch tube 37 is pinched off to prevent fluid flow therethrough.

Fluid volume through the dispensing tube is controlled by means of a volumetric infusion pump 17. The volumetric infusion pump 17 accurately maintains constant flow through the dispensing tube 16 and can regulate the amount of fluid administered. By controlling the amount of fluid administered while the appropriate valve is open the volume of solution dispensed is automatically controlled.

Accurate control of fluid administration may be assured by sequentially opening and closing the valves 40 so that a single volumetric infusion pump may be used to draw fluids from each of the solution bottles sequentially. A volumetric infusion pump is capable of metering the amount of solution administered to a patient. When none of the medications are required the valve 40 controlling the trunk tube 32 is opened to permit the keep open solution or base solution to flow, thereby keeping the intravenous needle open and free of clots. The valve 40 for the keep open solution is preferably opened for a short period between changes in medication to flush out the manifold, thereby preventing intermixing of different solutions.

The present invention may also be used with a heparin lock unit by semi-ambulant patients.

Since the supply tubes 14 of the present invention are hooked up to the apparatus 10 and do not need to be sheathed and unsheathed periodically to administer medication, the supply tubes 14 may be tied together out of the way of the hospital staff and the patient.

According to the present invention the tubing manifold 22 is disposable thereby eliminating the need to clean and sterilize the manifold apparatus between uses on different patients. The valve plate 23 is easily disassembled from the manifold plate 20 and the tubing manifold may be simply disconnected from the supply tubes 14 and removed from the manifold plate 21. The tubing manifold 22 is then replaced when a new patient is to be hooked up to the manifold unit. This procedure assures that a patient will not inadvertently receive residue from inside a manifold as was possible with prior art manifold units. The branch tubes 37 are received in the trunk tube at a slight angle which inhibits solutions from intermixing in the branch tubes 37 and supply tubes 14.

In the disclosed embodiment of the invention, up to eight solutions may be accommodated by a single manifold apparatus 10. It should be understood that the number of branches and valves provided can be changed without departing from the scope of the invention. Each of the fluids is introduced into the trunk tube at a location spaced from the other openings 38 in the trunk tube 32. In this way the fluids are introduced into the trunk tube and begin flowing toward the bottom 28 of the manifold plate 21 before encountering the next opening 38 in the trunk tube 32. This arrangement prevents the fluids from intermixing and contaminating one another.

The invention has been described with reference to two preferred embodiments and it is to be understood that the foregoing description is intended to be exemplary. Various modifications are possible within the spirit and scope of the invention. The scope of the present invention should be determined by reference to the appended claims.

I claim:

1. A manifold assembly adapted for administering a plurality of different intravenous solutions comprising:
   a manifold plate having a pair of generally flat inner and outer surfaces, a pair of side surfaces and a pair of end surfaces, an elongated slot provided in said inner surface and extending from one end surface to the other end surface, said slot being of generally U-shape configuration;
   a plurality of branch slots provided in said inner surface and extending from said elongated slot to said side surfaces of the manifold plate; some of said branch slots extending to one side surface and the remaining branch slots extending to the other side surface;
   said branch slots being of generally U-shape configuration;
   a disposable tubing manifold made of flexible tubing and having a trunk tube disposed in said elongated slot and a plurality of branch tubes equal in number to the number of branch slots disposed in said branch slots, with one branch tube in a branch slot, each branch tube being connected to the trunk tube on a first end and extending from the trunk tube towards one or the other side surface, said branch tubes being connected to said trunk tube to permit fluid flow from the branch tubes to the trunk tube;
   female tubing connector means attached to one end of said trunk tube and a second end of each branch tube for attachment with a male connector of a solution supply tube;
   means attached to the other end of said trunk tube for attaching the manifold to an intravenous solution supply tube;
   a valve plate having a pair of generally flat inner and outer surfaces, with the inner surfaces of the manifold and valve plates abutting and attached together thereby enclosing said elongated slot and branch slots;
   a plurality of valves mounted in said valve plate, with each of said valves having a clamp means movable towards and away from said tubing manifold for selectively engaging and thereby closing said branch tubes and said trunk tube to prevent fluid flow therethrough;
   and means for releasing said clamp means to selectively permit fluid flow therethrough.

2. In the manifold assembly of claim 1, wherein said valve plate and said manifold plate are separable, to permit said tubing manifold to be removed from the manifold plate and replaced.

3. In the manifold assembly of claim 1, wherein the branch slots in said manifold plate extend from said elongated slot to define an acute angle between the portion of the elongated slot extending towards said one end surface and each branch slot.

4. In the manifold assembly of claim 1, wherein said control means is a threaded shaft having a wedge at a first end for engaging said tubing and a knob at a second end for turning the shaft to move the shaft relative to a fixed threaded packing nut.

5. In the manifold assembly of claim 1, wherein said intravenous solution supply tube is connected to a volumetric infusion pump which urges said solutions into a patient.

6. In the manifold assembly of claim 1, wherein said releasing means permits fluid flow through only one of said valves at a time to permit accurate measuring of fluid flow therethrough.

7. A disposable plastic tubing manifold comprising:
   an elongated and flexible trunk tube having on one end a female connector and on the other end a male connector;
   a plurality of flexible branch tubes connected on their inner ends to opposing surfaces of said elongated trunk tube for fluid flow, said branch tubes being of generally equal length and extending in a direction away from the trunk tube, parallel to one another each of said branch tubes extending from said trunk tube in longitudinally spaced relationship from the other of said branch tubes; and
   each of said branch tubes having a female tubing connector on the outer end thereof.

8. In the tubing manifold of claim 7, wherein said branch tubes extend perpendicularly away from said elongated tube.

* * * * *